US012758742B2

(12) United States Patent
Hitzeroth et al.

(10) Patent No.: US 12,758,742 B2
(45) Date of Patent: Oct. 13, 2026

(54) SHEATH VALVE HOUSING

(71) Applicant: Biosense Webster (Israel) Ltd., Yokneam (IL)

(72) Inventors: Matthew W. Hitzeroth, Irwindale, CA (US); Raymond Yue-Sing Tang, Rosemead, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 932 days.

(21) Appl. No.: 17/970,086

(22) Filed: Oct. 20, 2022

(65) Prior Publication Data

US 2023/0140352 A1 May 4, 2023

Related U.S. Application Data

(60) Provisional application No. 63/272,849, filed on Oct. 28, 2021.

(51) Int. Cl.

*A61M 25/00* (2006.01)
*A61M 39/06* (2006.01)
*A61M 39/22* (2006.01)
*A61M 39/00* (2006.01)

(52) U.S. Cl.

CPC .... *A61M 25/0097* (2013.01); *A61M 25/0068* (2013.01); *A61M 2039/0081* (2013.01); *A61M 2039/062* (2013.01); *A61M 39/22* (2013.01)

(58) Field of Classification Search

CPC .. A61M 2039/0081; A61M 2039/0072; A61M 2039/0036; A61M 25/0097; A61M 2206/10; A61M 2206/11

USPC .......................................................... 604/27

See application file for complete search history.

(56) References Cited

U.S. PATENT DOCUMENTS

| | | | | | |
|---|---|---|---|---|---|
| 2012/0245511 | A1* | 9/2012 | Stearns | A61B 17/3423 | 604/26 |
| 2013/0090608 | A1 | 4/2013 | Stout et al. | | |
| 2014/0350471 | A1* | 11/2014 | Schultz | A61B 17/3415 | 604/171 |
| 2015/0190570 | A1* | 7/2015 | Teoh | A61M 39/0613 | 29/428 |

(Continued)

FOREIGN PATENT DOCUMENTS

| | | | | |
|---|---|---|---|---|
| EP | 3892868 A1 * | 10/2021 | G01F 15/00 |
| WO | 2009016184 A1 | 2/2009 | |

(Continued)

OTHER PUBLICATIONS

Extended European Search Report and Opinion dated Mar. 27, 2023, from corresponding European Application No. 22204209.5.

*Primary Examiner* — Jason E Flick
*Assistant Examiner* — Isabella S North

(57) ABSTRACT

A sheath valve housing including: an input port disposed on a proximal side of the sheath valve housing; an output port disposed on a distal side of the sheath valve housing, the input port and output port defining a longitudinal axis extending therethrough; a chamber disposed within the sheath valve housing between the input port and the output port and centered on the longitudinal axis, a catheter pathway being defined within the sheath valve housing through the chamber between the input port and the output port; and a plurality of ribs disposed about the chamber so that a member is aligned with the longitudinal axis upon insertion into the chamber.

16 Claims, 13 Drawing Sheets

(56) References Cited

U.S. PATENT DOCUMENTS

| | | | | |
|---|---|---|---|---|
| 2016/0038700 | A1* | 2/2016 | White | A61M 39/22<br>128/205.19 |
| 2019/0262598 | A1* | 8/2019 | Mock | A61M 39/06 |
| 2020/0023166 | A1 | 1/2020 | Burkholz et al. | |

FOREIGN PATENT DOCUMENTS

| | | | | |
|---|---|---|---|---|
| WO | WO-2010151507 | A1 * | 12/2010 | A61M 39/26 |
| WO | 2021095873 | A1 | 5/2021 | |
| WO | WO-2021166643 | A1 * | 8/2021 | A61M 39/0247 |

* cited by examiner

SHEATH VALVE HOUSING

CROSS REFERENCE TO RELATED APPLICATIONS

This application claims the benefit of priority under 35 U.S.C. § 119 to prior filed U.S. Provisional Patent Application No. 63/272,849 filed on Oct. 28, 2021, the entire contents of which is hereby incorporated by reference as if set forth in full herein.

FIELD

The present application relates generally to catheters, and specifically to sheath valve housings.

BACKGROUND

Catheters are used in various medical and surgical procedures, including ablation, such as arrhythmia ablation, mapping, such as cardiac mapping, and drug delivery, such as intracardial drug delivery. One danger of catheters is the potential for an air embolism caused by the unintentional introduction of air into a patient's circulatory system at an insertion site. In the related art, either extremely slow and careful insertion of the catheter or jetting (e.g., over-pressurization of a valve housing) are used to mitigate this risk. However, these mitigation efforts require active effort on the part of an operation team.

Thus, structural mechanisms of reducing the risk of air embolisms are desired in the art.

SUMMARY

A sheath valve housing is included herein, which includes: an input port disposed on a proximal side of the sheath valve housing; an output port disposed on a distal side of the sheath valve housing, the input port and output port defining a longitudinal axis extending therethrough; a chamber disposed within the sheath valve housing between the input port and the output port and centered on the longitudinal axis, a catheter pathway being defined within the sheath valve housing through the chamber between the input port and the output port; and a plurality of ribs disposed about the chamber so that a member is aligned with the longitudinal axis upon insertion into the chamber.

In any of the examples disclosed herein, at least one rib of the plurality of ribs may have at least one cutout.

In any of the examples disclosed herein, at least one of the at least one cutout may be between about one-fourth and one-half of a length of the at least one rib.

In any of the examples disclosed herein, at least one of the at least one cutout may be about one-third the length of the rib.

In any of the examples disclosed herein, at least one cutout being between about one-half and three-fourths of a length of the rib.

In any of the examples disclosed herein, at least one of the at least one cutout may be about two-thirds the length of the rib.

In any of the examples disclosed herein, at least one of the at least one cutout may be on an edge of the catheter pathway.

In any of the examples disclosed herein, at least one of the at least one cutout may be an internal hole through the at least one rib.

In any of the examples disclosed herein, at least one of the at least one cutout may be on an edge of the at least one rib closest to a body of the chamber.

In any of the examples disclosed herein, the sheath valve housing may further include an aspiration port connected to the chamber.

In any of the examples disclosed herein, at least one of the plurality of ribs may have a cutout creating a fluid pathway on a perimeter of the chamber to the aspiration port.

In any of the examples disclosed herein, the plurality of ribs may be positioned substantially parallel to the catheter pathway.

In any of the examples disclosed herein, the plurality of ribs may be slanted inwardly along the catheter pathway.

In any of the examples disclosed herein, the chamber may be slanted inwardly along the catheter pathway.

In any of the examples disclosed herein, the sheath valve housing may further include a secondary wall formed about a distal end of the plurality of ribs.

In any of the examples disclosed herein, the sheath valve housing may further include a valve body and a cap, the cap forming the input port.

In any of the examples disclosed herein, the plurality of ribs may provide a guidance mechanism to a catheter through the catheter pathway.

According to aspects of the present disclosure, there is provided a method of using a using a sheath valve housing, the method including providing a sheath valve housing according to any of the foregoing, attaching the sheath valve housing to a sheath; inserting a catheter through the catheter pathway via the input port such that the catheter is centered on the longitudinal axis by the plurality of ribs in the chamber; and aspirating the catheter through the aspiration port.

According to aspects of the present disclosure, there is provided a method of using a using a sheath valve housing, the method including providing a sheath valve housing including an input port disposed on a proximal side of the sheath valve housing, an output port disposed on a distal side of the sheath valve housing, the output port and input port defining a longitudinal axis extending therethrough; a chamber disposed within the sheath valve housing between the input port and the output port, a catheter pathway being aligned with the longitudinal axis and defined within the sheath valve housing through the chamber between the input port and the output port; a plurality of ribs disposed about the chamber; and an aspiration port connected to the chamber; attaching the sheath valve housing to a sheath; inserting a catheter through the catheter pathway via the input port such that the catheter is centered on the longitudinal axis by the plurality of ribs in the chamber; and aspirating the catheter through the aspiration port.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

Figure 1A:
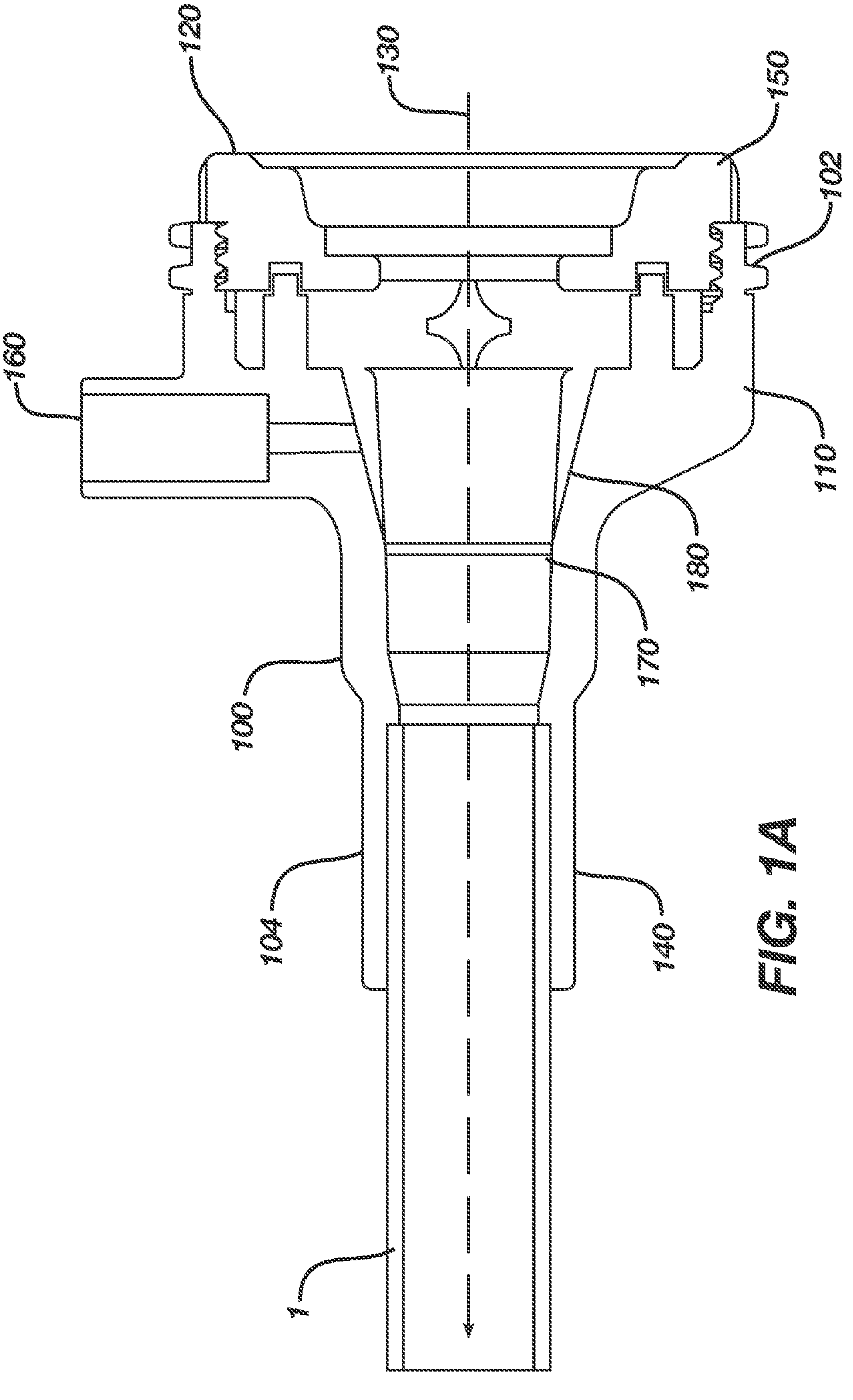
FIG. 1A illustrates a side cross-sectional view of a sheath valve housing connected to a sheath according to aspects of the present disclosure.

The following description of certain examples of the disclosure should not be used to limit the scope of the present disclosure. The drawings, which are not necessarily to scale, depict selected embodiments and are not intended to limit the scope of the disclosure. The detailed description illustrates by way of example, not by way of limitation, the principles of the disclosure. Other examples, features, aspects, embodiments, and advantages of the disclosure will become apparent to those skilled in the pertinent art from the following description, which includes, by way of illustration, one of the best modes contemplated for carrying out the disclosure. As will be realized, the disclosure is capable of other different or equivalent aspects, all without departing from the disclosure. Accordingly, the drawings and descriptions should be regarded as illustrative in nature and not restrictive.

The following-described teachings, expressions, versions, examples, etc., should therefore not be viewed in isolation relative to each other. Various suitable ways in which the teachings herein may be combined are apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

As used herein, the terms "comprising" or "containing" or "including" are interpreted to mean that at least the named compound, element, particle, or method step is present in the composition or article or method, but does not exclude the presence of other compounds, materials, particles, method steps, even if the other such compounds, material, particles, method steps have the same function as what is named.

As used herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

Ranges described as being between a first value and a second value are inclusive of the first and second values, as well as all values therebetween. Likewise, ranges described as being from a first value and to a second value are inclusive of the first and second values, as well as all values therebetween.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after the development of the presently disclosed subject matter.

Reference will now be made in detail to examples of the disclosed technology, such as those illustrated in the accompanying drawings. Wherever convenient, the same references numbers will be used throughout the drawings to refer to the same or like parts.

FIG. 1A illustrates an example sheath valve housing 100, attached to a sheath 1. Sheath valve housing 100 has a valve body 110 with proximal end 102 and a distal end 104. Valve body 110 includes an input port 120 (e.g., a catheter input port 120) and an output port 140 (e.g., catheter output port 140) defining a catheter pathway 130 extending therethrough. The catheter pathway 130 may be a longitudinal axis 130 of the sheath valve housing 100. A cap 150 may be on a proximal end of the valve body 110. Input port 120 may be formed within cap 150. Cap 150 may be removably connectable to the proximal end of valve body 110 by, for example, press-fit and/or a screw fit. Cap 150 may be configured to form a sealed connection with valve body 110.

The valve body 110 may further include a chamber 170 disposed along the catheter pathway 130. Chamber 170 may be centered on the longitudinal axis 130. An aspiration port 160 may extend from chamber 170 to an exterior of sheath valve housing 100. Aspiration port 160 may be used to withdraw air from chamber 170 introduced, for example, through input port 120. A plurality of ribs 180 may be disposed about chamber 170. The ribs 180 may be substantially aligned with the catheter pathway 130. The ribs 180 provide an irrigation pathway to allow air to naturally coalesce within chamber 170 and move out of an irrigation pathway through aspiration port 160. In some cases, an inner wall of ribs 180 may be slanted inwardly along the catheter pathway 130, which may help guide a catheter from the input port 120 to the output port 140 along the catheter pathway 130. As non-limiting examples, the angle of the slant may be between about 10 and 40 degrees from parallel and, more particularly, between about 10 and 30, 10 and 20, 20 and 30, 20 and 40, 30 and 40, 10 and 15, 15 and 20, 20 and 25, 25 and 30, 30 and 35, or 35 and 40 degrees from parallel. In some cases, the slant may be about 30 degrees from parallel. Ribs 180 may sit substantially perpendicular to a radial direction of catheter pathway 130, or may be slanted outward such that bottom edges of ribs 180 are longitudinally closer to outlet port 140 than inward bottom edges of ribs 180.

Figure 1C:
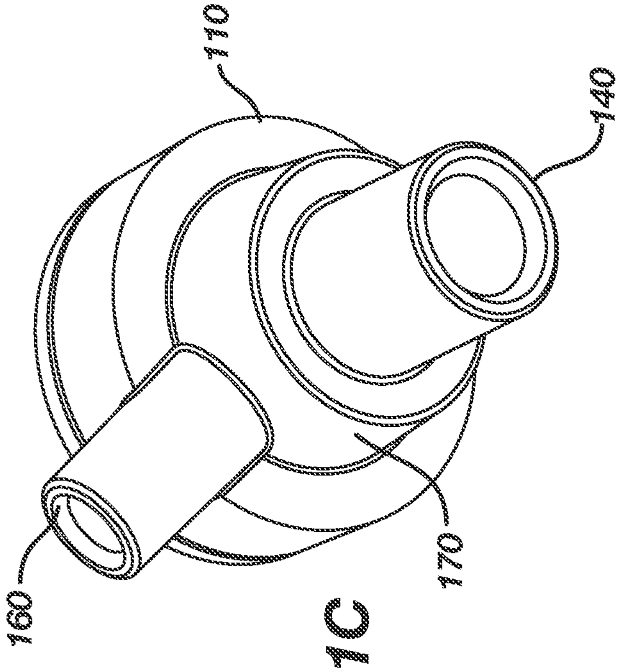
FIG. 1C is a perspective view of a sheath valve housing according to aspects of the present disclosure.
Figure 1D:
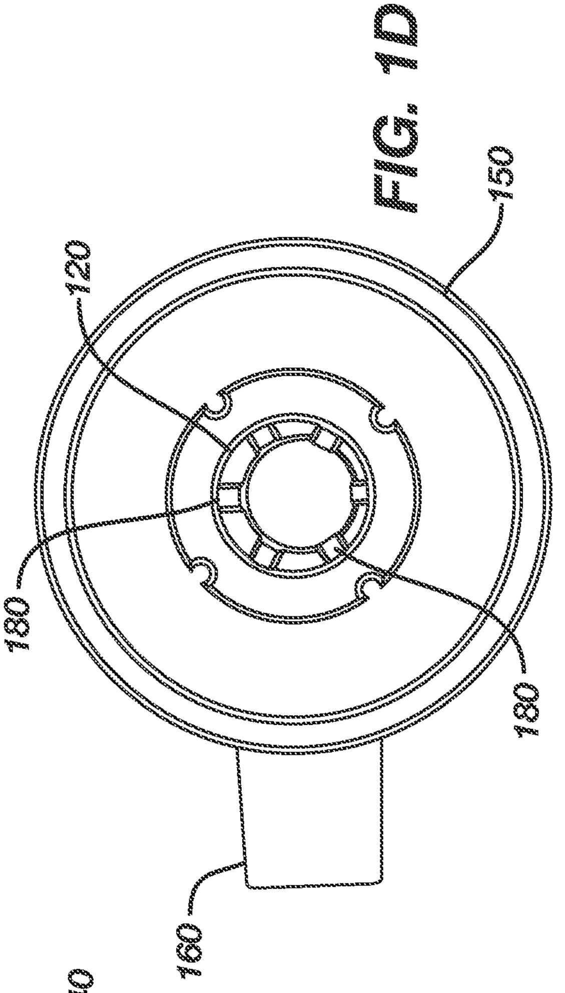
FIG. 1D is a planar view of a sheath valve housing facing according to aspects of the present disclosure
Figure 1B:
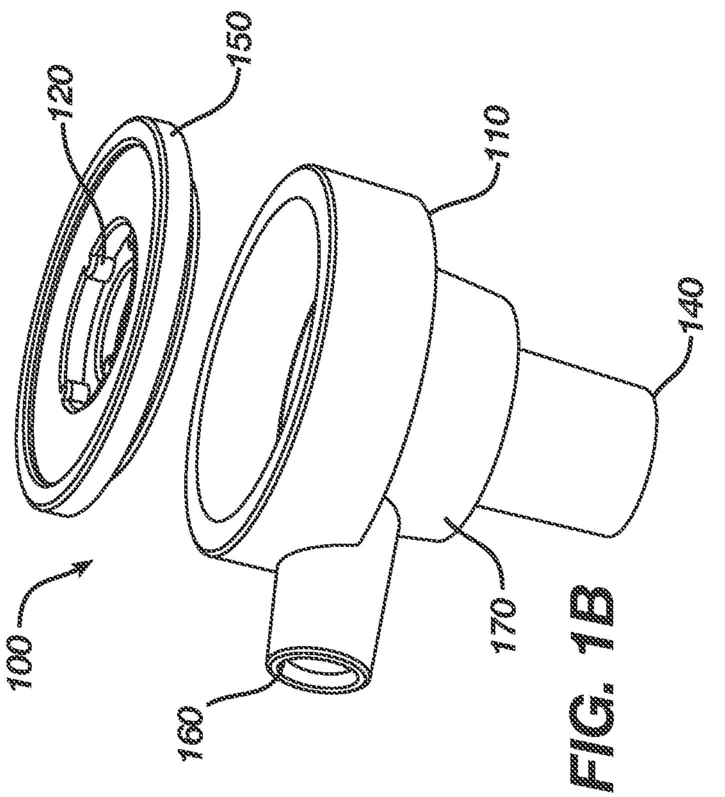
FIG. 1B is an exploded view of a sheath valve housing according to aspects of the present disclosure.

FIG. 1B illustrates a perspective view of sheath valve housing 100 with output port 140 pointing roughly down, aspiration port 160 pointing roughly leftward, and with cap 150 floating above valve body 110. FIG. 1C illustrates a perspective view of valve housing 100 looking towards output port 140. FIG. 1D illustrates a perspective view of valve housing 100 looking towards input port 120 and cap 150.

Figure 2B:
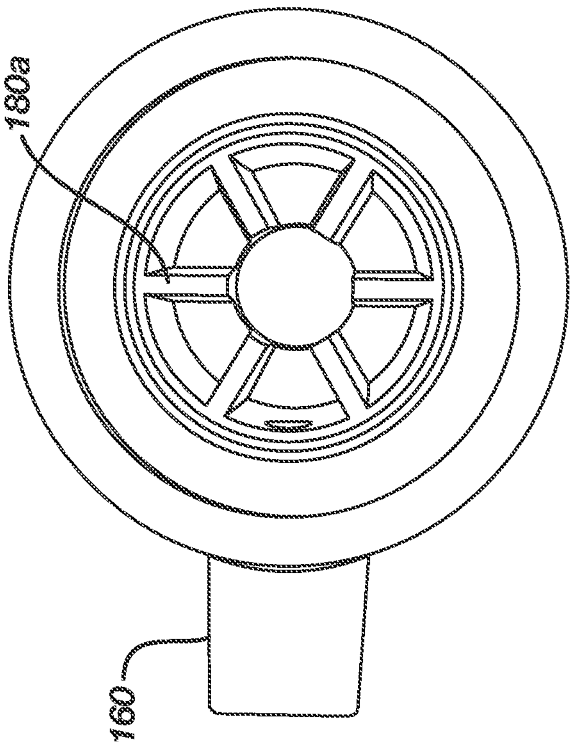
FIG. 2B is an interior view of a sheath valve housing according to aspects of the present disclosure.
Figure 2A:
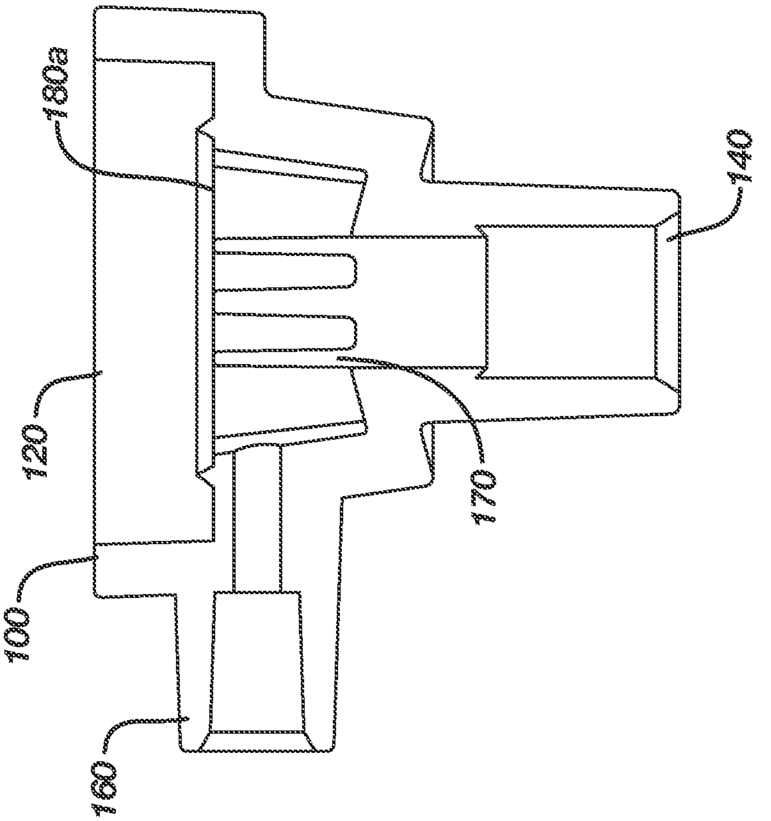
FIG. 2A is a side cross-sectional view of a sheath valve housing according to aspects of the present disclosure.

FIG. 2A illustrates a cutaway view of valve housing 100. FIG. 2B illustrates a top-down view of valve housing 100 with cap 150 removed. As can be seen in FIGS. 2A and 2B, six ribs 180*a* are substantially monolithic and evenly spaced around chamber 170. However, this is merely an example, and various changes to a number, distribution, or constitution of the ribs 180 may be made without departing from the scope of the present disclosure.

Figure 3B:
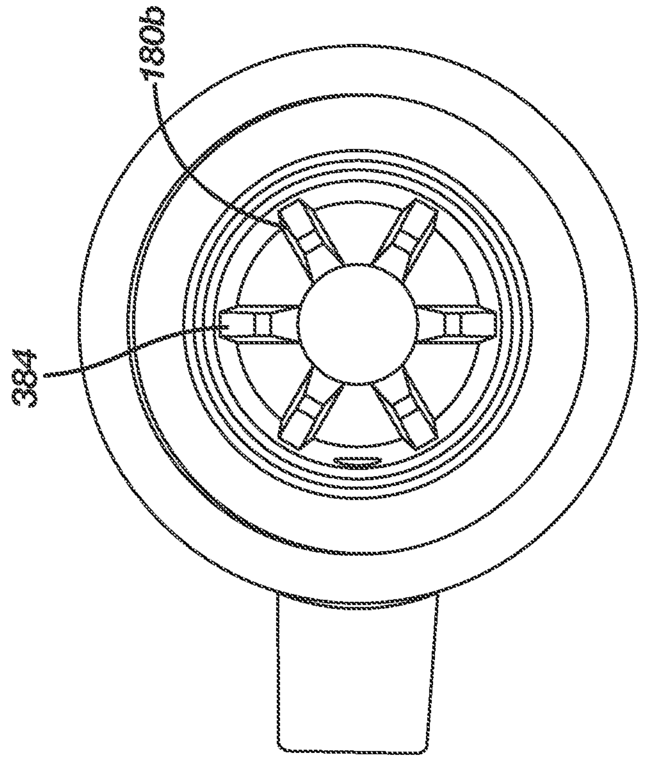
FIG. 3B is an interior view of a sheath valve housing according to aspects of the present disclosure.
Figure 3A:
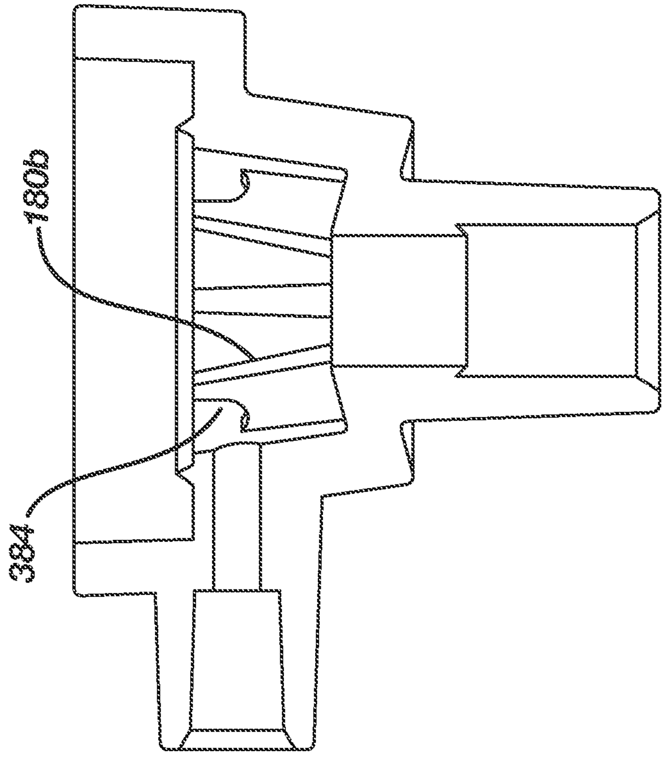
FIG. 3A is a side cross-sectional view of a sheath valve housing according to aspects of the present disclosure.

FIG. 3A illustrates a cutaway view of valve housing 100. FIG. 3B illustrates a top-down view of valve housing 100 with cap 150 removed. As can be seen in FIGS. 3A and 3B, six ribs 180*b* include cutouts 384 between about one-fourth and one-half a length of ribs 180*b*, for example, about one-third a length of ribs 180*b*. Cutouts 384 may help form a channel for air to move from chamber 170 to aspiration port 160. In FIGS. 3A and 3B, six ribs with substantially similar sizes and cutouts are spaced substantially evenly around chamber 170. However, this is merely an example, and various changes to a number, distribution, or constitution of the ribs 180 may be made without departing from the scope of the present disclosure.

Figure 4B:
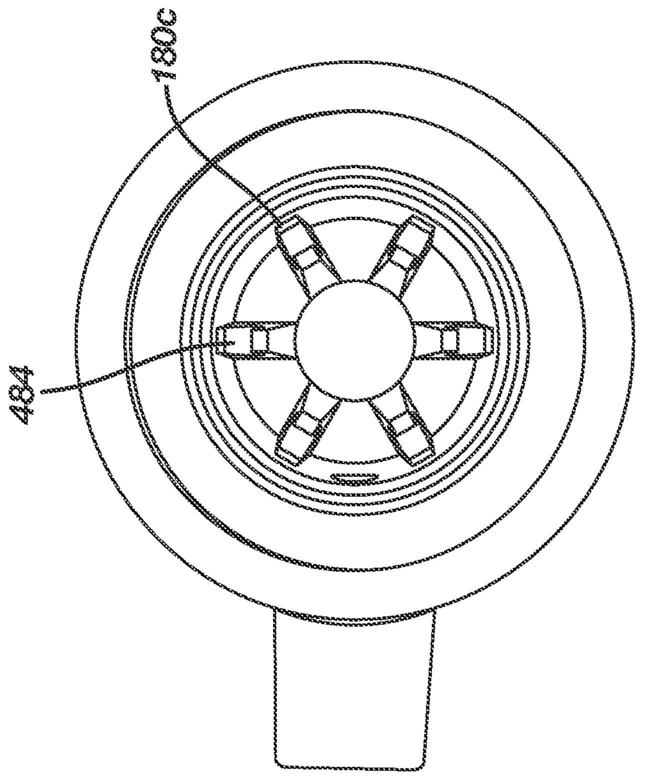
FIG. 4B is an interior view of a sheath valve housing according to aspects of the present disclosure.
Figure 4A:
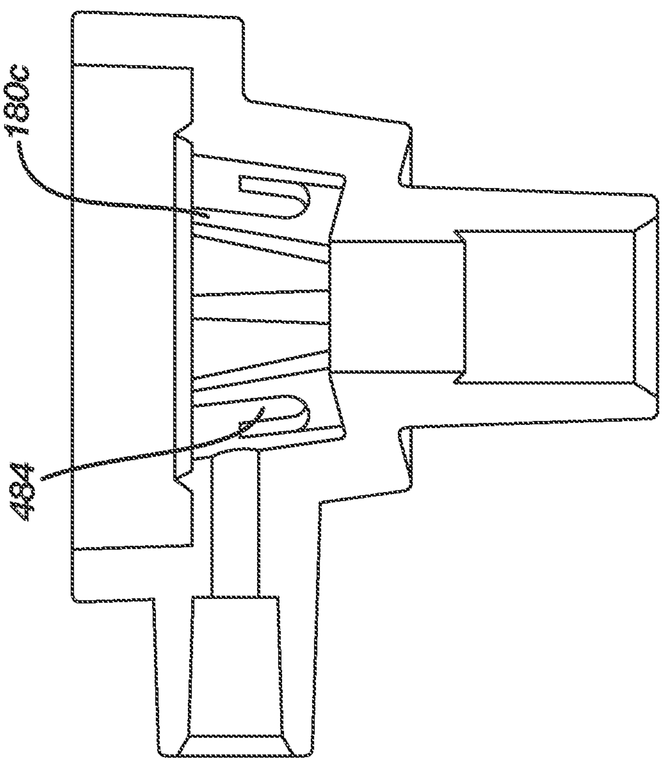
FIG. 4A is a side cross-sectional view of a sheath valve housing according to aspects of the present disclosure.

FIG. 4A illustrates a cutaway view of valve housing 100. FIG. 4B illustrates a top-down view of valve housing 100 with cap 150 removed. As can be seen in FIGS. 4A and 4B, six ribs 180*c* include cutouts 484 between about one-half and three-fourths a length of ribs 180*c*, for example, about two-thirds a length of ribs 180*c*. Cutouts 484 may help form a channel for air to move from chamber 170 to aspiration port 160. In FIGS. 4A and 4B, six ribs with substantially similar sizes and cutouts are spaced substantially evenly around chamber 170. However, this is merely an example, and various changes to a number, distribution, or constitution of the ribs 180 may be made without departing from the scope of the present disclosure.

Figure 5B:
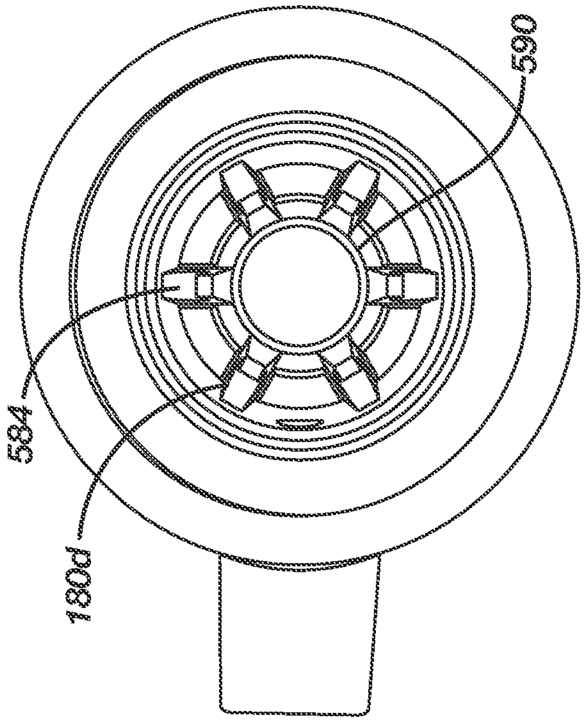
FIGS. 5B and 5C are interior views of a sheath valve housing according to aspects of the present disclosure.
Figure 5A:
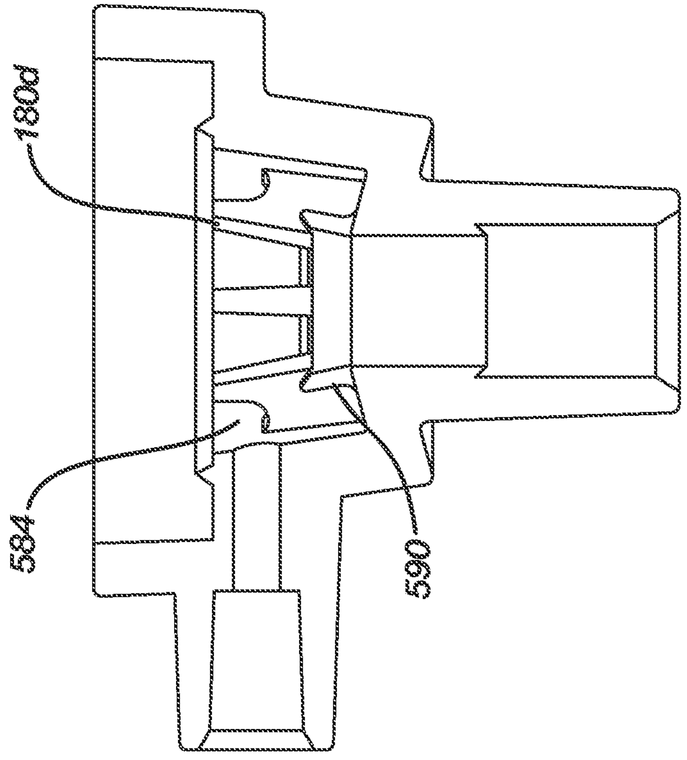
FIG. 5A is a side cross-sectional view of a sheath valve housing according to aspects of the present disclosure.
Figure 5C:
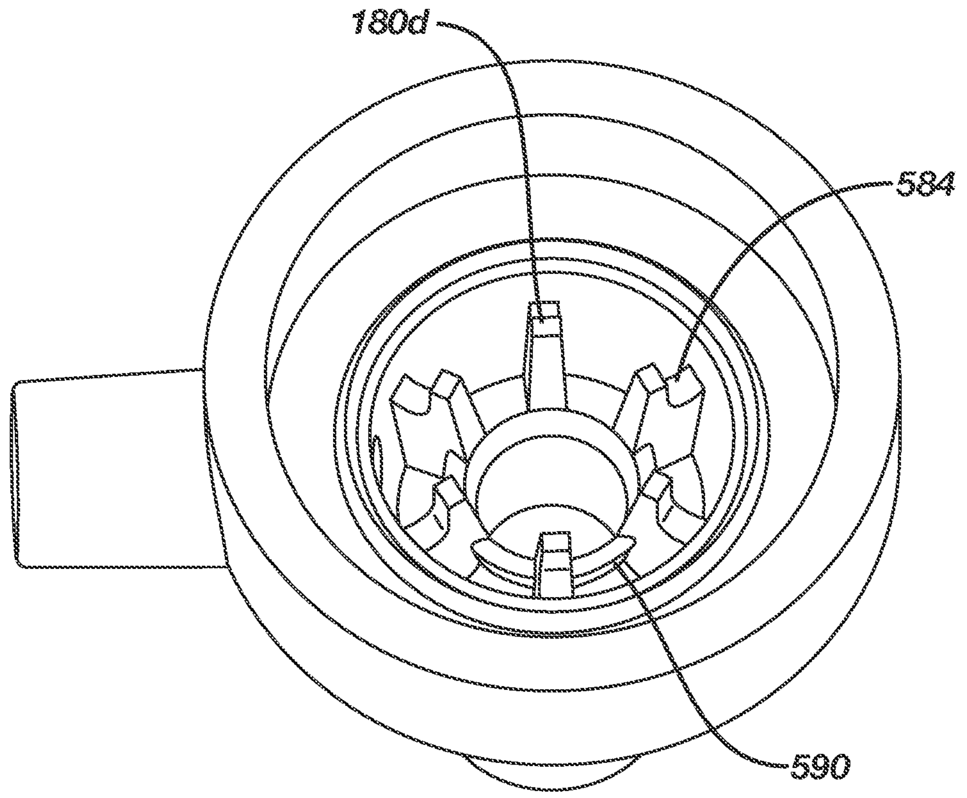

FIG. 5A illustrates a cutaway view of valve housing 100. FIG. 5B illustrates a top-down view of valve housing 100 with cap 150 removed. FIG. 5C illustrates a perspective view of valve housing 100 with cap 150 removed. As can be seen in FIGS. 5A-5C, six ribs 180*d* include cutouts 584 about one-third a height of ribs 180*d*. Cutouts 584 may be substantially similar to cutouts 384. Additionally, a secondary wall 590 is formed at a base of ribs 180*d* around and an outlet from chamber 170 to outlet port 140. Secondary wall 590 may further assist in retaining air bubbles within chamber 170 are they are directed to aspiration port 160. In some cases, the secondary wall 590 may be about 60 percent or less of the height of ribs 180*d*, and, more particularly, less than about 5, 10, 15, 20, 25, 30, 35, 40, 45, 50, or 55 percent or less of the height of ribs 180*d*. In some cases, the secondary wall 590 may be between about 5 and 60 percent of the height of ribs 180, and, more particularly, between about 5 and 10, 10 and 15, 15 and 20, 20 and 25, 25 and 30, 35 and 40, 45 and 50, 50 and 55, and 55 and 60 of the height of ribs 180*d*. In some cases, the secondary wall may be about 50 degrees of the height of ribs 180*d*. In some cases, secondary wall 590 may be flanged outwardly at a portion nearer the inlet port. As non-limiting examples, the angle of the flange may be between about 5 and 50 degrees from parallel and, more particularly, between about 10 and 30, 10 and 20, 20 and 30, 20 and 40, 30 and 40, 40 and 50, 5 and 10, 10 and 15, 15 and 20, 20 and 25, 25 and 30, 30 and 35, 35 and 40, 40 and 45, or 45 and 50 degrees from parallel. In some cases, the flange may be about 30 degrees from parallel.

In FIGS. 5A-5C, six ribs with substantially similar sizes and cutouts are spaced substantially evenly around chamber 170. However, this is merely an example, and various changes to a number, distribution, or constitution of the ribs 180 may be made without departing from the scope of the present disclosure. For example, substantially monolithic ribs 180*a* or ribs with an increased cutout (e.g., 180*b*) may be used with secondary wall 590. Additionally, various changes can be made to secondary wall 590, as illustrated without departing from the scope of the present disclosure.

Figure 6:
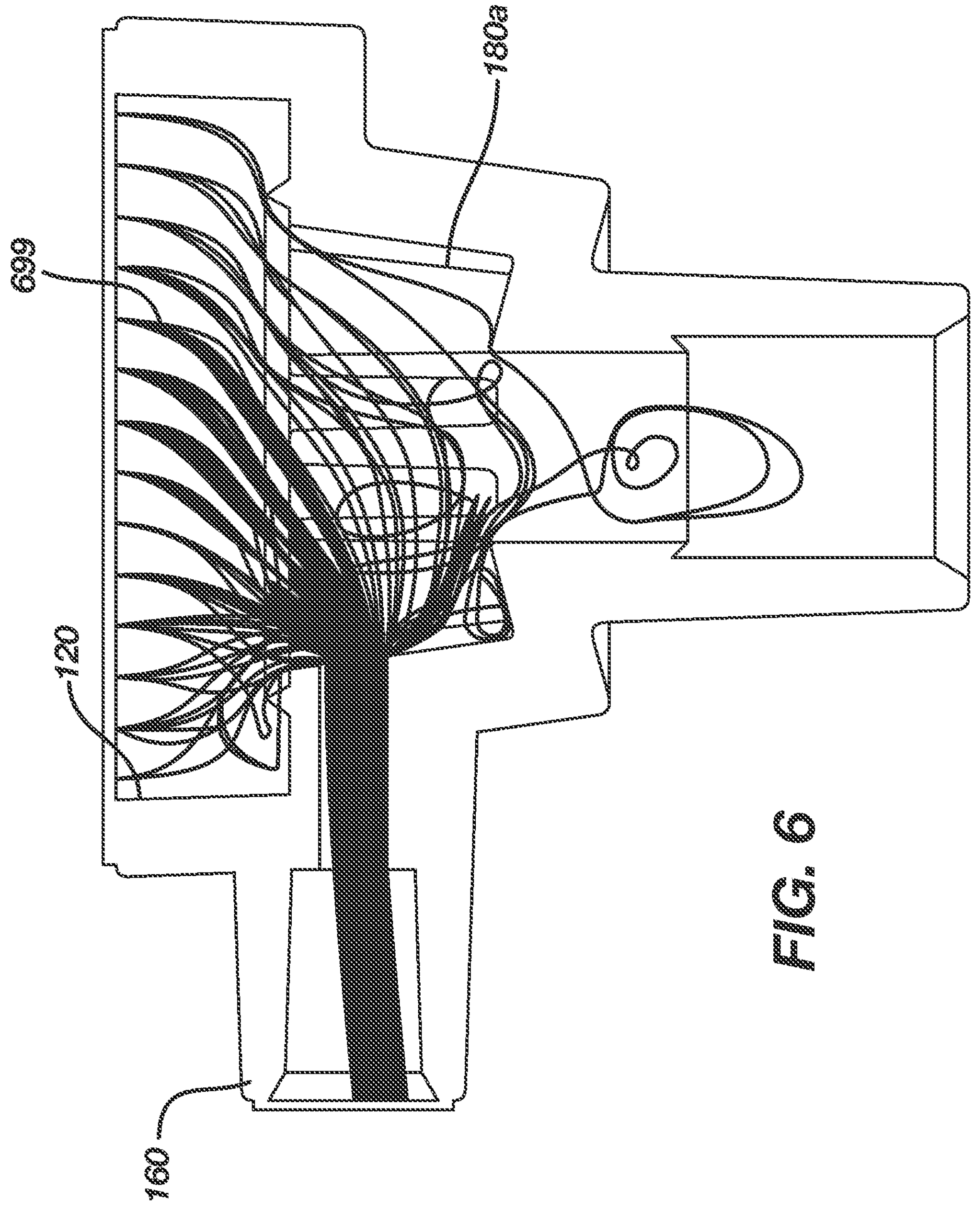
FIGS. 6-8 illustrates airflows in sheath valve housings according to aspects of the present disclosure.

FIG. 6 illustrates an example airflow 699 in a sheath valve housing 100 according to aspects of the present disclosure. As can be seen, the flow trajectories show that the ribs 180*a* 384 allow for liquid and air bubbles to flow when aspirating through aspiration port 160.

Figure 7:
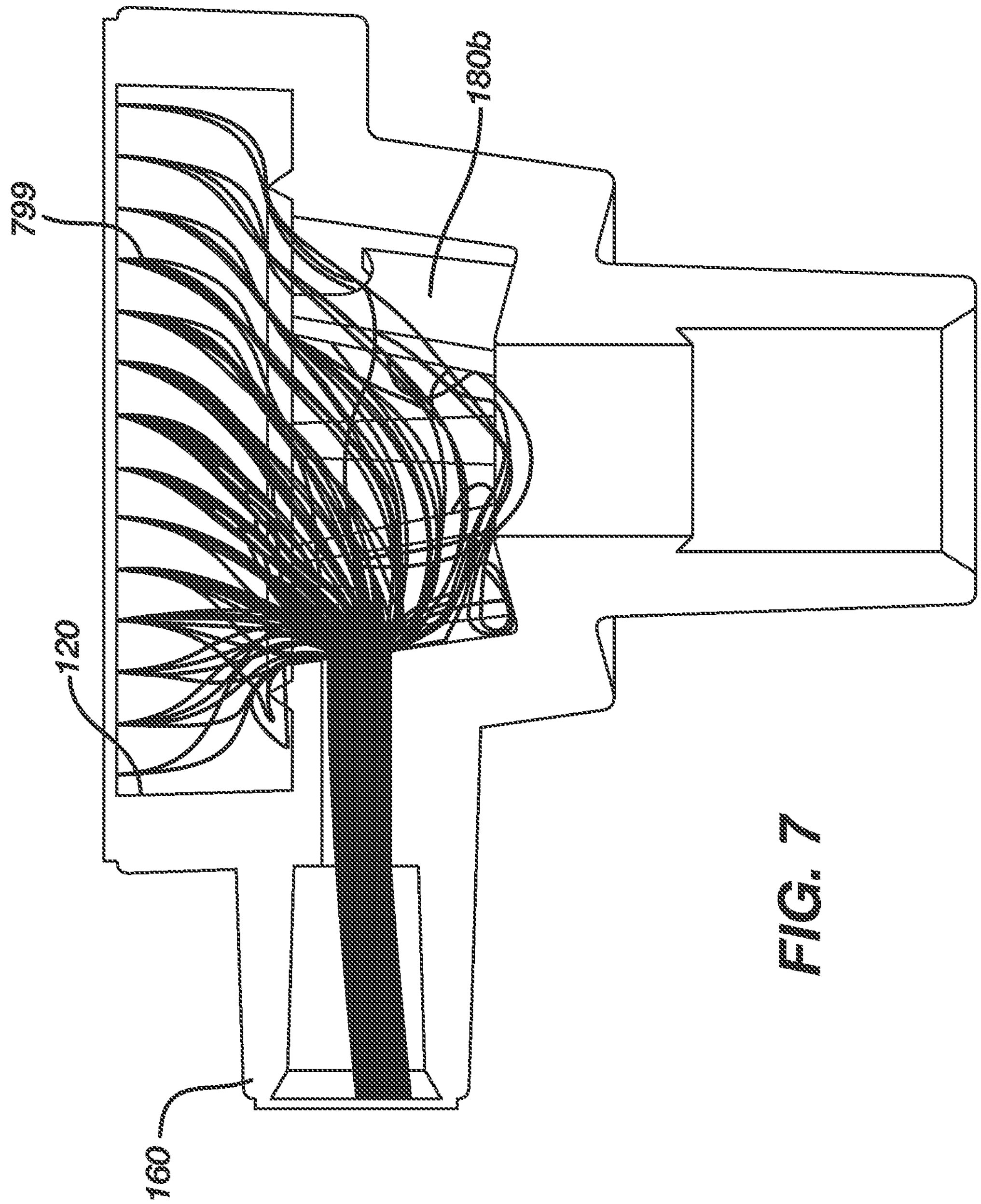

FIG. 7 illustrates an example airflow 799 in a sheath valve housing 100 according to aspects of the present disclosure. As can be seen, the flow trajectories show that the ribs 180*b* with cutouts 384 allow for liquid and air bubbles to flow thru when aspirating through aspiration port 160.

Figure 8:
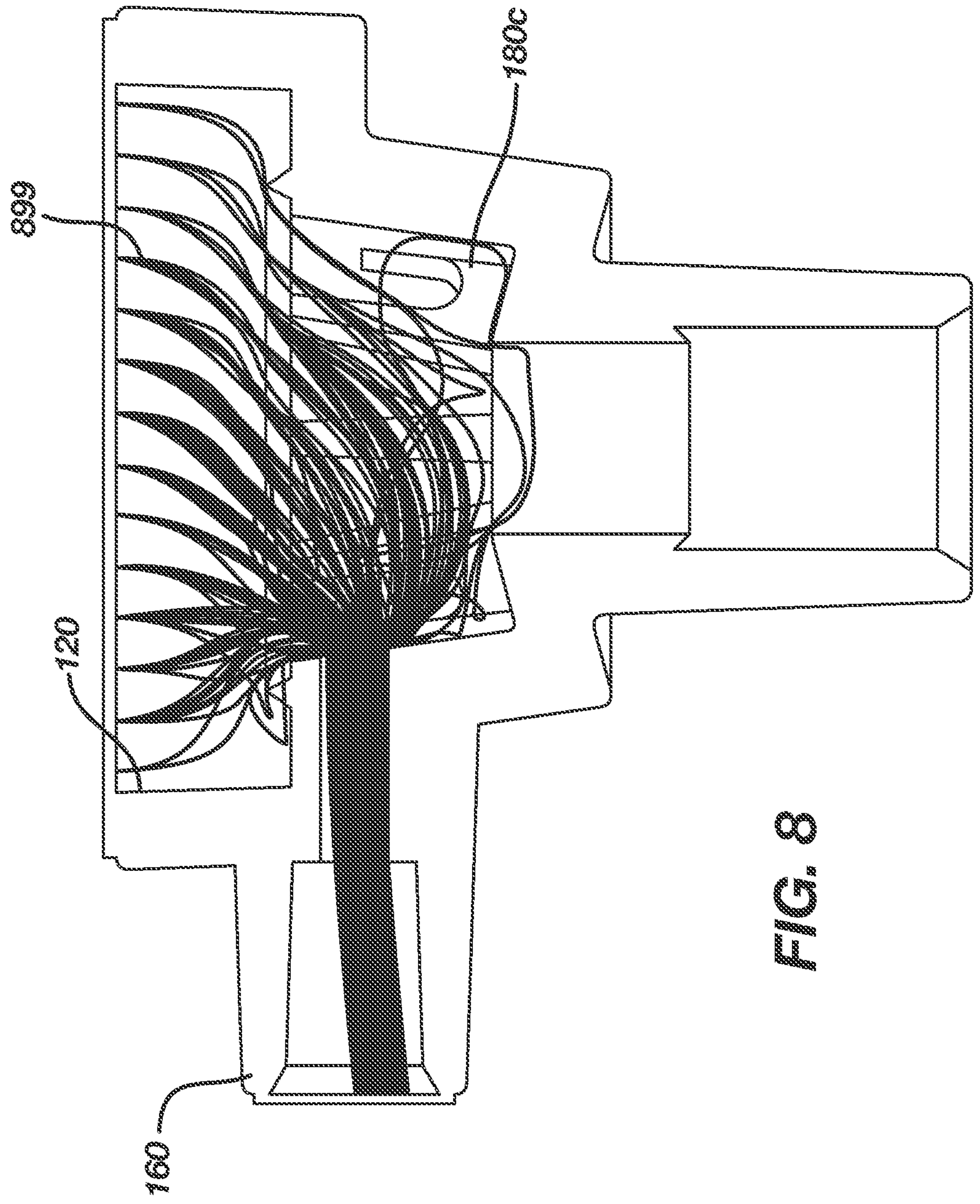

FIG. 8 illustrates an example of airflow 899 in a sheath valve housing 100 according to aspects of the present disclosure. As can be seen, the flow trajectories show that the ribs 180*c* with cutouts 484 allow for liquid and air bubbles to flow thru when aspirating through aspiration port 160. In some cases, openings within ribs (e.g., cutouts 384 or 484) may improve the flow trajectories.

Figure 9A:
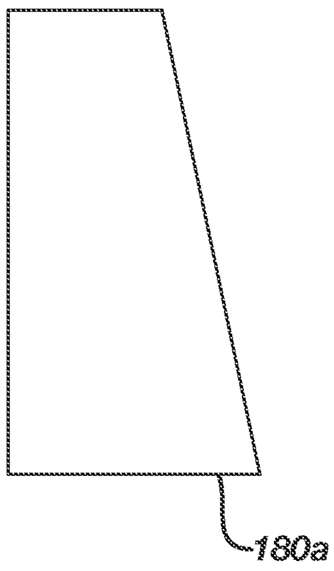
FIGS. 9A-9H illustrate example rib designs according to aspects of the present disclosure.
Figure 9B:
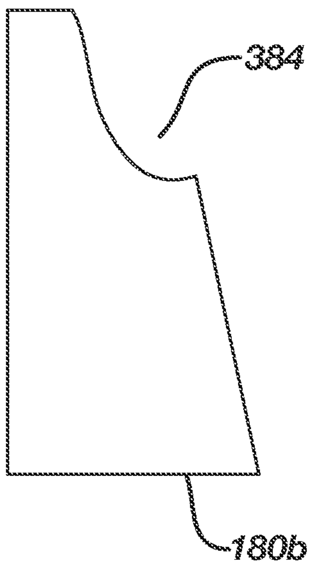
Figure 9C:
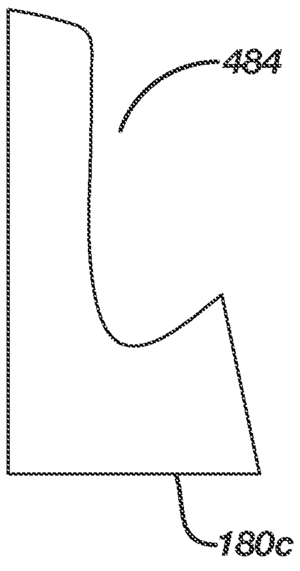
Figure 9D:
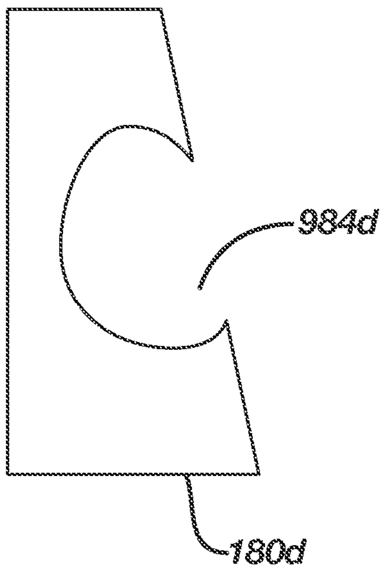
Figure 9E:
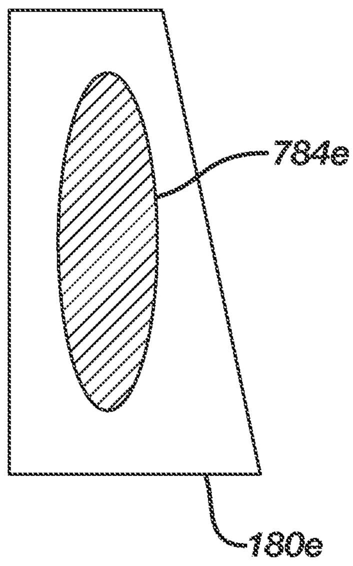
Figure 9F:
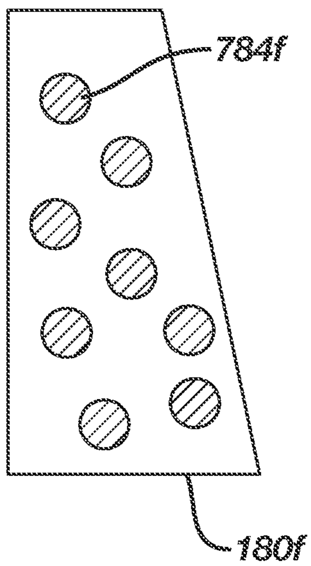
Figure 9G:
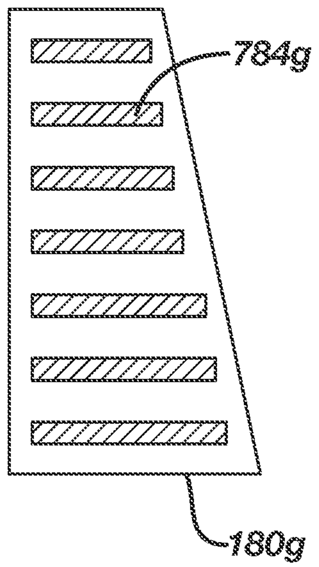
Figure 9H:
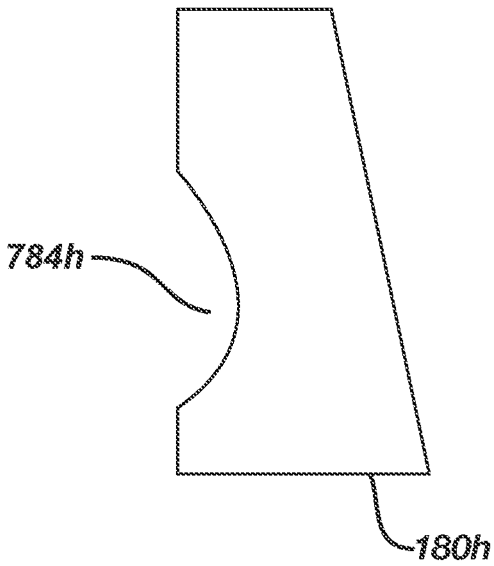

FIGS. 9A-9H illustrate different rib designs 180*a*-180*h* according to example embodiments. Referring to FIG. 9A, rib 180*a* is substantially monolithic and solid. Referring to FIG. 9B, rib 180*b* includes a cutout 384 about one-third of the way down rib 180*b*. Referring to FIG. 9C, rib 180*c* includes a cutout 484 about two-thirds of the way down rib 180*c*. Referring to FIG. 9D, rib 180*d* includes a cutout 984*d* halfway down a side of 180*d*, but is substantially monolithic and solid at top and bottom edges. Referring to FIG. 9E, rib 180*e* includes a cutout 984*e* through an interior portion go rib 180*e* (e.g., an internal hole). Cutout 984*e* may be substantially ovular, but this is merely an example. Referring to FIG. 9F, rib 180*f* includes a plurality of cutouts 984*f* through an interior portion go rib 180*f*. Cutouts 984*f* may be substantially circular, and of a substantially similar size and shape. However, this is merely an example. Referring to FIG. 9G, rib 180*g* includes a plurality of slots 984*g* through an interior portion go rib 180*g*. Slots 984*g* may be substantially rectangular with substantially even heights and varying lengths. However, this is merely an example. Referring to FIG. 9H, rib 180*h* includes a cutouts 984*h* on an edge of the rib 180*h* closest to catheter pathway 130 (e.g., on an interior edge of rib 180*h*).

One of ordinary skill will recognize in light of the present disclosure that various alternative rib designs may be used. Additionally, example features of multiple ribs 180*a*-180*h* may be combined. For example, a rib 180 may include an exterior-edge cutout 384, an interior cutout 984*e*, and an interior-edge cutout 984*h*. Furthermore, various rib designs may be used within a same sheath valve housing 100. For example, ribs 180 farther from aspiration port 160 may have more and/or larger cutouts than ribs 180 closest to aspiration port 160, but this is merely an example.

Figure 10:
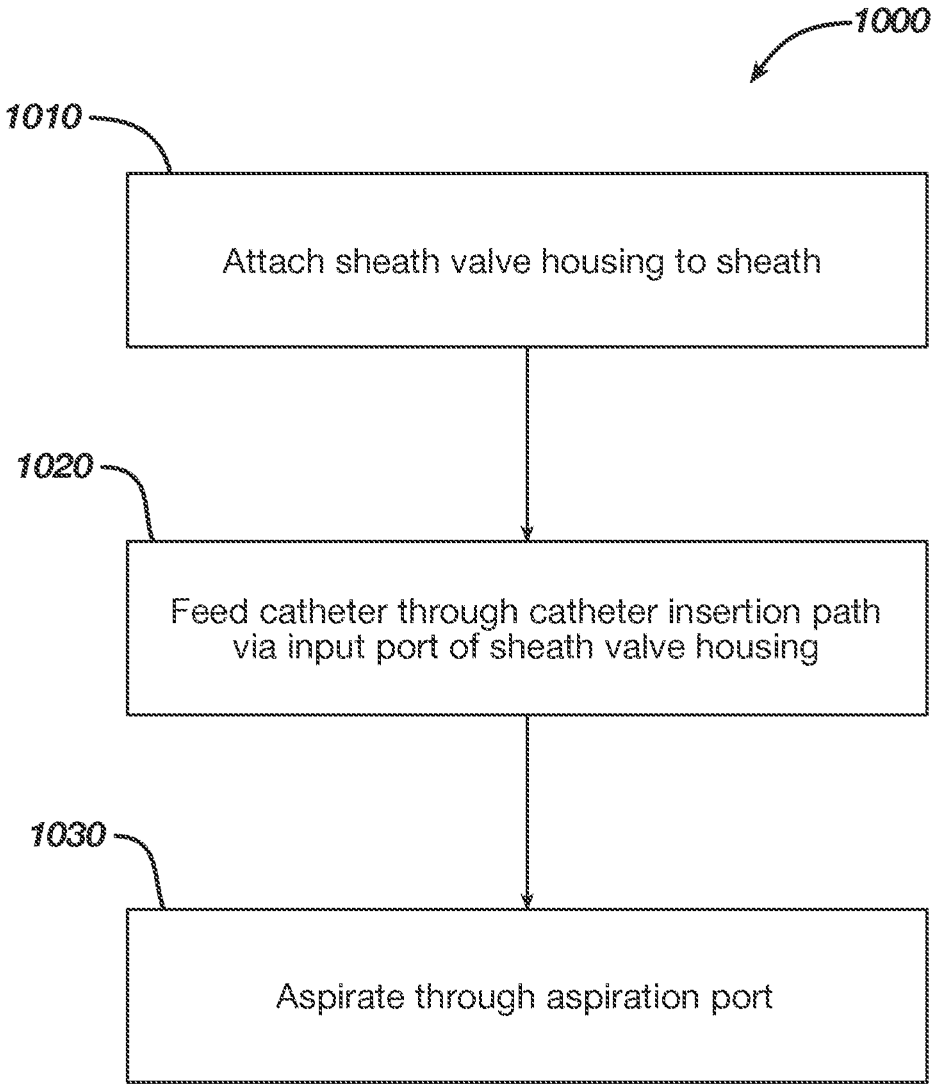
FIG. 10 is a flowchart of a method of creating a sheath valve housing according to aspects of the present disclosure.

FIG. 10 is a flowchart of a method 1000 of using a sheathe valve housing 100 according to aspects of the present disclosure. The method may be performed, for example, by a medical professional. The method may include attaching 1010 sheath valve housing 100 to a sheath 1. The method could include inserting 1010 an end of a sheath 1 into output port 140. Sheath 1 may already be inserted within a patient, e.g., within a patient's arteries.

Once sheath 1 is connected to sheath valve housing 100, a catheter may be fed through catheter insertion path 130 via input port 120 of sheath valve housing 100. That is, a distal end of the catheter may move from exterior to a patient, through input port 120, through chamber 170, and through outlet port 140 into sheath 1. Sheath 1 may be used to guide the catheter to a destination site within the patient.

Finally, when the catheter is being inserted 1020 and/or after the catheter has been inserted, sheath valve housing 100 is aspirated through aspiration port 160 at 1030. For example, a suction machine may be connected to aspiration port 160 to draw air and/or other fluids from chamber 170 to prevent them from entering a patient.

The descriptions contained herein are examples of embodiments and are not intended in any way to limit the scope of the invention. As described herein, the invention contemplates many variations and modifications of system components, including alternative combinations of components illustrated in separate figures, alternative materials, alternative component geometries, and alternative component placement. Modifications and variations apparent to those having skill in the pertinent art according to the teachings of this disclosure are intended to be within the scope of the claims which follow.

What is claimed is:

1. A sheath valve housing comprising:

an input port disposed on a proximal side of the sheath valve housing;

an output port disposed on a distal side of the sheath valve housing, the input port and output port defining a longitudinal axis extending therethrough;

a chamber disposed within the sheath valve housing between the input port and the output port and centered on the longitudinal axis, the chamber being at least partially defined by an inner surface of the sheath valve housing that faces towards the longitudinal axis, a catheter pathway being defined within the sheath valve housing through the chamber between the input port and the output port; and a plurality of ribs (i) disposed about the chamber on the inner surface, (ii) protruding inwardly into the chamber toward the longitudinal axis, and (iii) configured such that, when a member is inserted through the catheter pathway and into the chamber, the member is aligned with the longitudinal axis upon insertion into the chamber, at least one of the ribs of the plurality of ribs including at least one cutout, each cutout of a respective rib forming a channel in the respective rib to permit fluid communication around the respective rib within the chamber.

2. The sheath valve housing of claim 1, at least one of the at least one cutouts being between about one-fourth and one-half of a length of the at least one rib.

3. The sheath valve housing of claim 1, at least one of the at least one cutout being between about one-half and three-fourths of a length of the at least one rib.

4. The sheath valve housing of claim 1, at least one of the at least one cutout being an internal hole through the at least one rib.

5. The sheath valve housing of claim 1, at least one of the at least one cutouts being on an edge of the at least one rib closest to the longitudinal axis.

6. The sheath valve housing of claim 1 further comprising an aspiration port connected to the chamber.

7. The sheath valve housing of claim 5, at least one of the at least one cutouts creating a fluid pathway on a perimeter of the chamber to the aspiration port.

8. The sheath valve housing of claim 7, the plurality of ribs being positioned substantially parallel to the catheter pathway.

9. The sheath valve housing of claim 7, the plurality of ribs slanted inwardly along the catheter pathway.

10. The sheath valve housing of claim 7, the chamber slanted inwardly along the catheter pathway.

11. The sheath valve housing of claim 1 further comprising a secondary wall formed about a distal end of the plurality of ribs.

12. The sheath valve housing of claim 1 further comprising a valve body and a cap, the cap forming the input port.

13. The sheath valve housing of claim 1, the plurality of ribs providing a guidance mechanism to a catheter through the catheter pathway.

14. A sheath valve housing comprising:

an input port disposed on a proximal side of the sheath valve housing, an output port disposed on a distal side of the sheath valve housing, the output port and input port defining a longitudinal axis extending therethrough;

a chamber disposed within the sheath valve housing between the input port and the output port, the chamber being at least partially defined by an inner surface of sheath valve housing that faces towards the longitudinal axis, a catheter pathway being aligned with the longitudinal axis and defined within the sheath valve housing through the chamber between the input port and the output port;

a plurality of ribs (i) disposed about the chamber on the inner surface and (ii) protruding inwardly into the chamber toward the longitudinal axis, at least one of the rib of the plurality of ribs including at least one cutout, each cutout of a respective rib forming a channel in the respective rib to permit fluid communication around the respective rib within the chamber; and an aspiration port connected to the chamber, the channel of each cutout creating a fluid pathway on a perimeter of the chamber to the aspiration port.

15. The sheath valve housing of claim 14 further comprising a valve body and a cap, the cap forming the input port.

16. A method of use of a sheath valve housing, the method comprising:

providing a sheath valve housing comprising:

an input port disposed on a proximal side of the sheath valve housing, an output port disposed on a distal side of the sheath valve housing, the output port and input port defining a longitudinal axis extending therethrough;

a chamber disposed within the sheath valve housing between the input port and the output port, the chamber being at least partially defined by an inner surface of sheath valve housing that faces towards the longitudinal axis, a catheter pathway being aligned with the longitudinal axis and defined within the sheath valve housing through the chamber between the input port and the output port;

a plurality of ribs (i) disposed about the chamber and protruding inwardly into the chamber toward the longitudinal axis, at least one rib of the plurality of ribs including at least one cutout that forms a channel in the at least one rib; and an aspiration port connected to the chamber;

attaching the sheath valve housing to a sheath;

inserting a catheter through the catheter pathway via the input port such that the catheter is centered on the longitudinal axis by the plurality of ribs in the chamber; and aspirating, via the aspiration port, liquid and gas from the chamber such that the liquid and gas flow through the at least one cutout along a fluid pathway on a perimeter of the chamber to the aspiration port.

* * * * *